United States Patent [19]

Elango et al.

[11] Patent Number: 5,380,648
[45] Date of Patent: Jan. 10, 1995

[54] METHOD FOR THE DIAGNOSIS OF VIRULENT BACTERIA

[75] Inventors: Shanmugam Elango; Shantha Rajarathnam; Vasanthi Ramachandran; Raman K. Roy; Krishnan Sankaran; Yerramilli V. B. Subrahmanyam, all of Bangalore, India

[73] Assignee: Aktiebolaget Astra, Sodertalje, Sweden

[21] Appl. No.: 504,945

[22] Filed: Apr. 5, 1990

[30] Foreign Application Priority Data

Apr. 5, 1989 [SE] Sweden ................................. 8901188

[51] Int. Cl.⁶ ..................... G01N 33/569; C07K 3/14; C12Q 1/02
[52] U.S. Cl. ................... 435/7.32; 435/7.37; 435/7.92; 435/7.95; 435/29; 435/32; 435/34; 530/412; 530/825
[58] Field of Search ........................ 435/7.2, 7.21, 7.32, 435/7.37, 30, 32, 34, 38, 259, 261, 849, 5, 7.22, 5, 7.33, 7.35, 7.94, 7.95, 29; 436/518, 519, 524, 528; 530/412, 417, 825

[56] References Cited

U.S. PATENT DOCUMENTS

| | | | |
|---|---|---|---|
| 4,299,916 | 11/1981 | Litman et al. | 435/6 |
| 4,497,899 | 2/1985 | Armstrong et al. | 436/510 |
| 4,775,621 | 10/1988 | Berkoff et al. | 435/38 |
| 4,851,330 | 7/1989 | Kohne et al. | 435/6 |

OTHER PUBLICATIONS

Ishiguro et al, J. Bacteriol., 164(3): 1233-1237 (Dec. 1985).
Tijssen, Practice and Theory of Enzyme Immunoassays, pp. 423-447, Elsevier (Amsterdam, New York, Oxford) (1985).
Qadri et al. "Congo Red Binding and Salt Aggregation as Indicators of Viradence in Shijella Species" Jo. Clin. Micro. vol. 26 No. 7 Jul. 1988 pp. 1343-1348.
Hale et al. "Identification and Antigenic Characterization of Virulence Associated, Plasmid-Coated Proteins of Shijella spp. and Enteroinasive E. coli" Infect. & Immun. vol. 50, No. 3 Dec. '85 pp. 620-629.
Hale et al. "Characterization of Virulence Plasmids and Plasmid-Associated Outer Membrane Proteins in Shigella Flexerni, Shigella Sonnei and E. coli" Infect and Immun. vol. 40, No. 1 Apr. '83 pp. 340-350.
Microbial Pathogenesis, vol. 4, 1988, Bernadette Baudry et al; "Nucleotide sequence of the invasion plasmid antigen B and C genes iipaB and ipaC) of Shigella Flexneri", pp. 345-357.
Journal of Bacteriology, vol. 169, No. 6, 1987, Jerry M. Buysse et al: "Molecular Cloning of Invasion Plasmid Antigen (ipa) Genes from Shigella flexneri: Analysis of ipa Gene Products and Genetic".
Infection and Immunity, vol. 55, No. 6, 1987, Panagiotis A. Daskaleros et al: "Congo Red Binding Phenotype Is Associated with Hemin Binding and Increased Infectivity of Shigella flexneri in the HeLa Cell Model", pp. 1393-1398.
Infectiion and Immunity, vol. 54, No. 2, 1986, Panagiotis A. Daskaleros et al: "Characterization of Shigella flexneri Sequences Encoding Congo Red Binding (crb): Conservation of Multiple crb Sequences and Role of IS1 in Loss of the Crb+ Phenotype", pp. 435-443.
Infection and Immunity, vol. 51, No. 2, 1986, Takashi Sakai et al: "Molecular Cloning of a Genetic Determinant for Conga Red Binding Ability Which Is Essential for the Virulence of Shigella".

*Primary Examiner*—Carol E. Bidwell
*Attorney, Agent, or Firm*—White & Case

[57] ABSTRACT

Induction of virulence related proteins in virulent pathogenic E. coli and Shigella by growing such bacteria in the presence of Congo Red as induction triggering factor, and the application of the induction for purposes of diagnosing virulent pathogens and their antibiotic sensitivity.

17 Claims, 8 Drawing Sheets

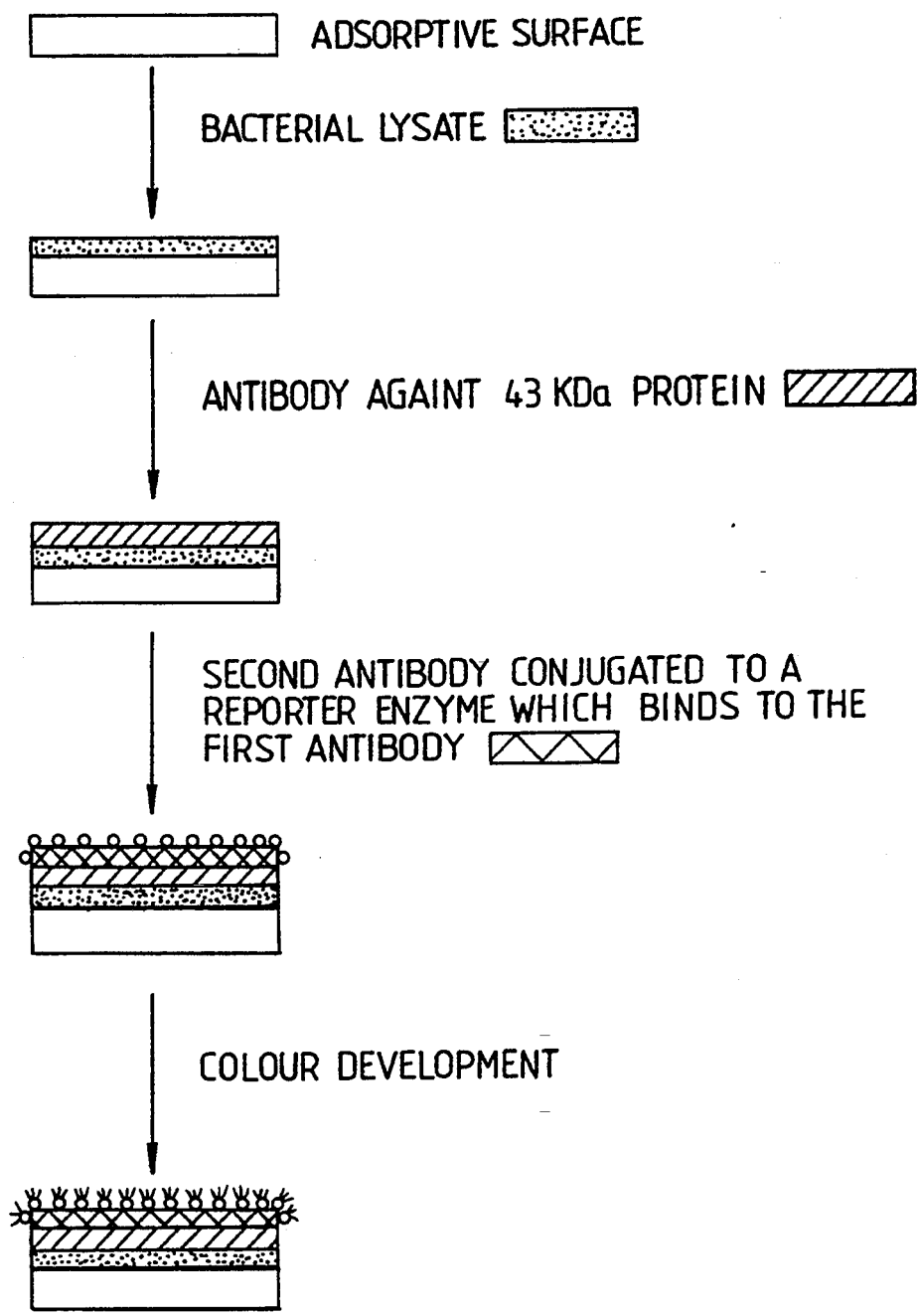

METHOD FOR THE DIAGNOSIS OF VIRULENT BACTERIA

BACKGROUND INFORMATION

Diarrhoea and dysentery are common enteric diseases which are fatal if they are not treated promptly. Dysentery caused by Shigella and other enteroinvasive pathogens like enteroinvasive *Escherichia coli* (EIEC) lead to high mortality and morbidity especially in children (WHO Report, 1986). Secondary complications such as haemolytic uraemic syndrome, colonic perforation are common. Of the enteropathogens Shigella is the most communicable; as few as ten organisms can cause dysentery in man. Enteroinvasive pathogens migrate to colonic epithelial cells, enter the colonic epithelial cells by inducing phagocytosis, multiply inside causing cell death and infect neighbouring cells (1). This results in tissue destruction, mucosal inflammation, epithelial ulceration and haemorrhage leading to the characteristic symptoms of dysentery, diarrhoea with blood and mucus.

The virulence of Shigella is not a very stable property. Mutants which are avirulent occur naturally and this can be achieved in laboratories simply by subculturing the virulent isolates (2). The virulent bacteria could be distinguished from avirulent bacteria by their ability to bind the dye, Congo red (CR) (3), to invade epithelial cells and to cause keratoconjunctivitis in guinea pig eye [Sereny test (2)]. Early studies employing classical genetics, identified a few major chromosomal loci (Purine, Xylose-Rhamnose, Glycerol kinase, Histidine and Maltose) as being responsible for expression of virulence in Shigella (4). However, only at the turn of this decade it became apparent that a large extra chromosomal genetic element (100–140 MDa) called megaplasmid is needed to code for the invasive phenotype of Shigella(5). It is clear that both chromosome and megaplasmid are necessary for the expression of total virulence (6) i.e. the ability to cause dysentery in man.

Detailed molecular genetic studies employing recombinant DNA techniques have led to the identification of several virulence related loci on the megaplasmid DNA. The virF locus confers the CR binding phenotype to the Shigella (7). The invasion plasmid antigen (ipa) genes B,C,D and A which encode polypeptides of 62 KDa, 42 KDa, 37 KDa and 78 KDa respectively are implicated in the invasion of the bacterium into colonic epithelial cells (8). Another locus virG is involved in conferring the ability to the bacterium to reinfect the neighbouring cells (9). The expression of these virulence genes is under thermoregulated factors (10). At 30° C. Shigella is not virulent and virulence phenotypes are not expressed (11).

PRIOR ART

CR has been routinely used to distinguish virulent from avirulent invasive organisms like Shigella, (3) (12) Yersinia, and Aeromonas (13). In a typical test, organisms are grown in agar plates containing 0.01% CR. The virulent bacteria form red colonies whereas the avirulent organisms form pale pink or white colonies. Moreover, the virulent colonies appear smaller than the avirulent ones, this being another phenotypic marker for virulence.

The existing practice of growing bacteria on agar plates containing CR or a CR binding assay in solution (14) does not allow one to derive a true picture of how CR affects the virulent and avirulent organisms differently, for, in the former one cannot obtain enough bacteria to do adequate (biochemical) investigations whereas in the latter the cells are not allowed to grow at all in the presence of CR. Without unequivocal verification it is believed that the dye associated with the virulent organisms is essentially in the bound form on the surface of the bacteria. Only in the case of Aeromonas has the actual CR binding protein been isolated with the CR binding property of the protein shown and its localization at the outer surface demonstrated (13). In the case of Shigella three putative CR binding proteins (relative molecular weight 21,000, 27,000, 30,000 daltons) have been implicated based on the amino acid sequence derived from the cloned 1 kb fragment on the megaplasmid (15). So far, there has been no isolation of these proteins and demonstration of the CR binding property. Taking the available evidence from the literature into consideration, it is not known till now how CR preferentially binds to the virulent bacteria. In the experience of the inventors no significant differences could be made out in the protein profiles of virulent and avirulent Shigella when analysed by sodium dodecyl sulphate-Polyacrylamide gel electrophoresis (SDS-PAGE) and staining by Coomassie blue. CR binding and invasive phenotypes have been found to be associated intimately, since bacteria which do not bind CR do not invade the epithelial cells (12). It has not been demonstrated so far that CR affects the regulation of virulence factors nor the regulatory regions involved has been identified. In Shigella no protein that binds CR has been either identified or isolated.

The multiple antibiotic resistance of these enteropathogens has added a new dimension to the problem of disease management. Since, oral rehydration therapy is not effective in dysentery it is imperative that antibiotic treatment is initiated soon to control the disease. Knowledge of antibiotic sensitivity is important to administer the proper antibiotic and avoid unwanted administration of antibiotics which are not effective against the organism. Serodiagnosis at the early stage (acute phase) is not possible while the conventional microbiological and biochemical identification techniques are laborious and time consuming. These tests take upto three days which prove critical in the treatment of the disease especially in infante. A rapid and specific test which also gives the antibiotic sensitivity pattern based on the virulence of Shigella is very important.

BRIEF DESCRIPTION OF THE DRAWINGS

FIGS. 7a and 7b are schematic representations ELISA techniques.

DETAILS OF INVENTION

By the present invention it has been demonstrated that:

1. Intracellular CR uptake is associated with the virulence phenotype and requires growth of the bacteria in the presence of CR at permissive temperatures.
2. Induction of three inner membrane proteins (63 KDa, 58 KDa and 43 KDa) is brought about as a consequence of CR uptake in the virulent phenotypes at the permissive temperature.
3. The induced proteins mentioned above are associated with pathogenesis of the virulent bacteria.

On the basis of these characterizations, a diagnostic procedure for the specific detection of virulent invasive bacteria in general and Shigella and EIEC in particular has been developed. The test can be designed to give the antibiotic sensitivity of the virulent bacteria at the same time.

The present invention has wide applications which are exemplified by but not limited to the diagnosis of diseases, epidemiological screening, forensic investigations, determination of food contamination, public health surveys, and in preventive medicine.

The term "induction" as used in the present specification shall mean de novo synthesis of a gene product such as a protein due to stimulation by an externally added agent, enhancement in the synthesis of the gene product, overproduction of the gene product, regulation of the expression of a gene product resulting in enhancement of its production, modulation of the process of gene expression leading to increase of production of the gene product, stimulation of processes subsequent to the gene expression leading to increased production or modification of any intermediate process leading to the production of the final product. The concept of specifically inducing a gene product or a group of gene products, has applications in the identification of living organisms including virulent pathogens such as bacteria, unicellular and multicellular organisms, parasites and viruses. Another aspect of the invention is to utilise the intracellular uptake of an externally added substance in virulent pathogen as a means of identification of the pathogen by detecting intracellularly incorporated external substance.

i. Demonstration that CR uptake is virulence associated

Figure 1:
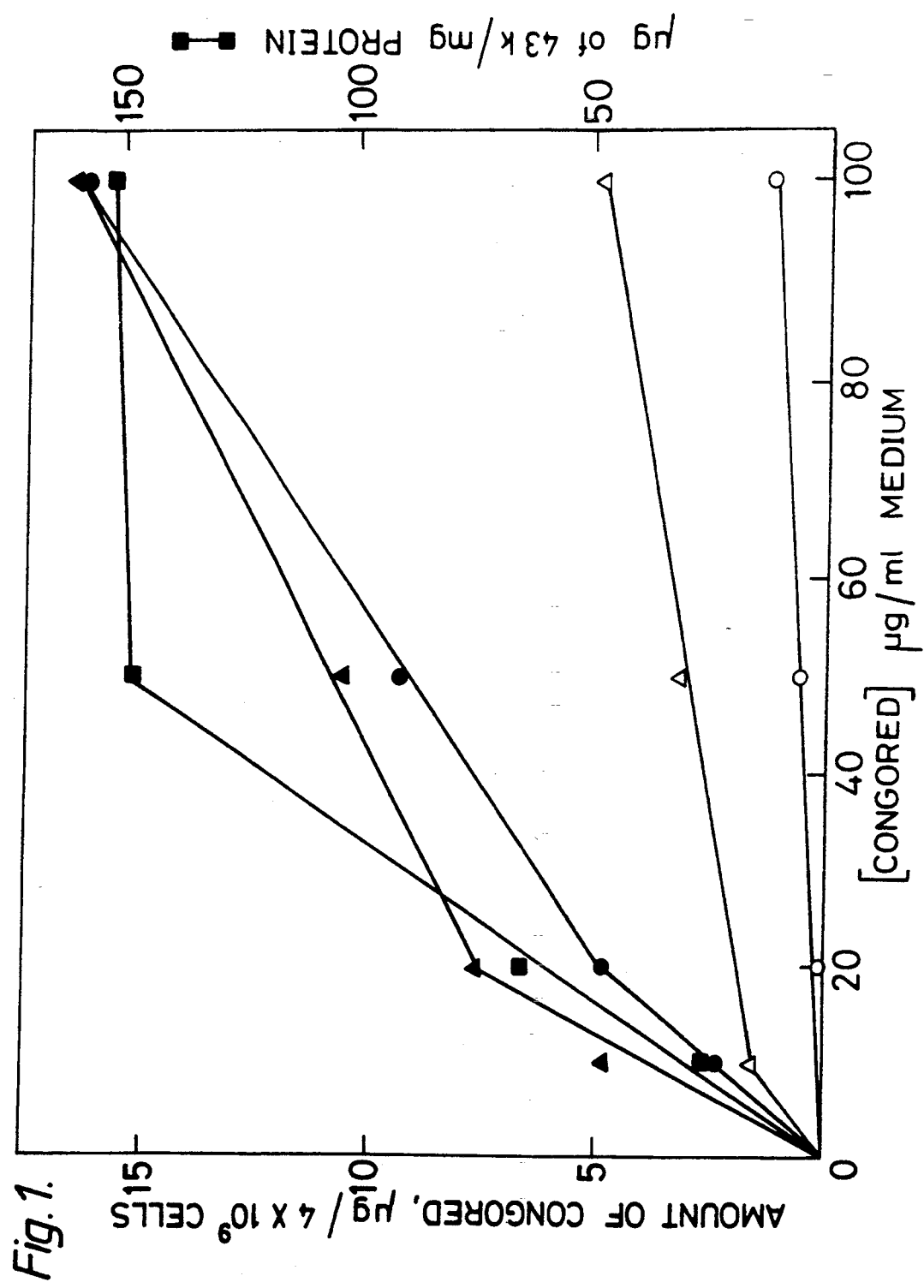
FIG. 1 shows uptake of Congo Red by virulent and avirulent Shigella.
Figures 1, 5A:
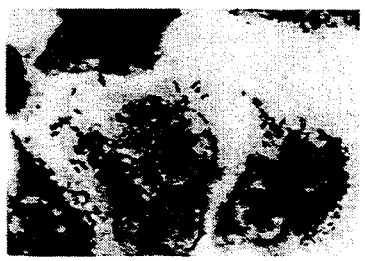
FIGS. 5A–5C show invasion of epithelial cells by *S. flexneri* and detection of 43 KDa proteins.
Figures 2, 5A:
Figures 3, 5A:
Figures 1, 5B:
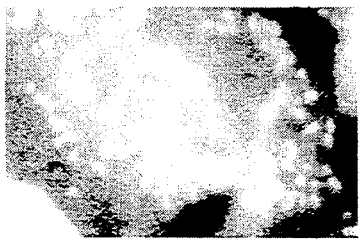
Figures 2, 5B:
Figures 3, 5B:
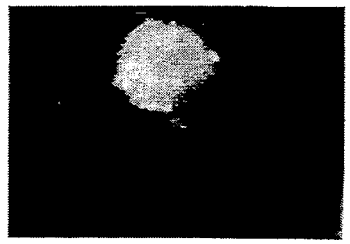
Figures 1, 5C:
Figures 2, 5C:
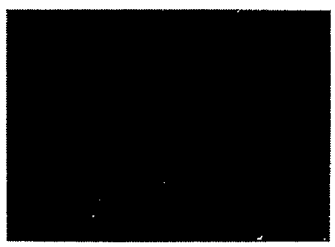
Figures 3, 5C:
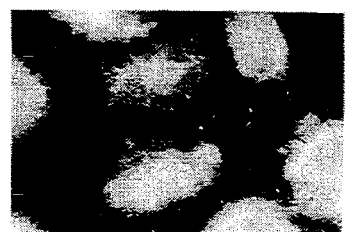

Bacteria were grown in presence of the dye, CR, in liquid phase, harvested at various time points of its growth and the cytosolic and membrane fractions were separated to verify whether the dye is just bound to the surface of the cells as generally thought or is also seen inside the cells. Our invention shows that CR is taken up in a virulent-associated manner. Virulent bacteria accumulate cytosolic CR to the extent of 45 $\mu g/10^{10}$ cells from medium containing 100 $\mu g/ml$ CR, while the avirulent isolate took up only 8.5 $\mu g/10^{10}$ cells (FIG. 1). When virulent Shiqella was grown at 30° C., a condition in which the virulence phenotype is not expressed, the amount of dye that was taken up was insignificant. The dye is transported across the bacterial membranes against the concentration gradient and is bound to macromolecular components of the cytosol. Although the ability to bind the dye is inherent in the cytosol irrespective of whether the Shiqella is virulent or avirulent the transport of the dye across the membrane is governed in a virulence associated manner (Example 1, Table 2). There is a membrane component which is expressed in virulent phenotypes that controls the entry of the dye. Intracellular uptake of CR reaches significant levels only at 5 hours and beyond (Example 1, Table 1) (FIG. 2). The amount of dye accumulated in the cytoplasm shows a linear relationship with the dye concentration in the medium (FIG. 1).

ii. Demonstration that three proteins 63 KDa, 58 KDa and 43 KDa are induced as a consequence of CR uptake This invention shows that the intracellular CR plays a significant role in the biochemistry of Shiqella. It is found that CR totally alters the inner membrane protein profile of only the virulent Shiqella but not that of the avirulent phenotype (Example 2 FIG. 2). Several proteins in the molecular weight range of 90-20 KDa which otherwise are barely detectable by SDS-PAGE become major components of the inner membrane, after growing the bacteria in the presence of CR. Among the induced proteins three of apparent molecular weights 63 KDa, 58 KDa and 43 KDa are the major ones, representing about 25% of the total inner membrane proteins (15% of 43 KDa, 8% of 63 KDa and 5% of 58 KDa). In the uninduced state they represent the basal levels, of about 2% of the inner membrane protein mass.

iii. Demonstration that the induced proteins (63 KDa, 58 KDa and 43 KDa) are associated with pathogenesis of virulent bacteria The invention shows that the proteins are associated with virulence. It is well known that in Shiqella, virulence is not expressed at 30° C. and this has been shown in this invention to be true even in the case of induction of proteins by CR. At another non permissive temperature for virulence i.e. 42° C. no perceivable alteration in the inner membrane protein profile was detected even though CR uptake was comparable to that at 37° C. (Example 2, FIG. 3). These observations indicate that apart from CR there are other thermoregulatory factors which are essential for the induction of the said proteins. It is known that CR binding and expression of virulence genes are under independent thermoregulatory factors (10). The uptake of CR and the induction of these proteins is well correlated. There is a linear relationship between the quantity of induced proteins and the concentration of CR upto 50 $\mu g/ml$ in the medium (FIG. 1).

Figure 4B:
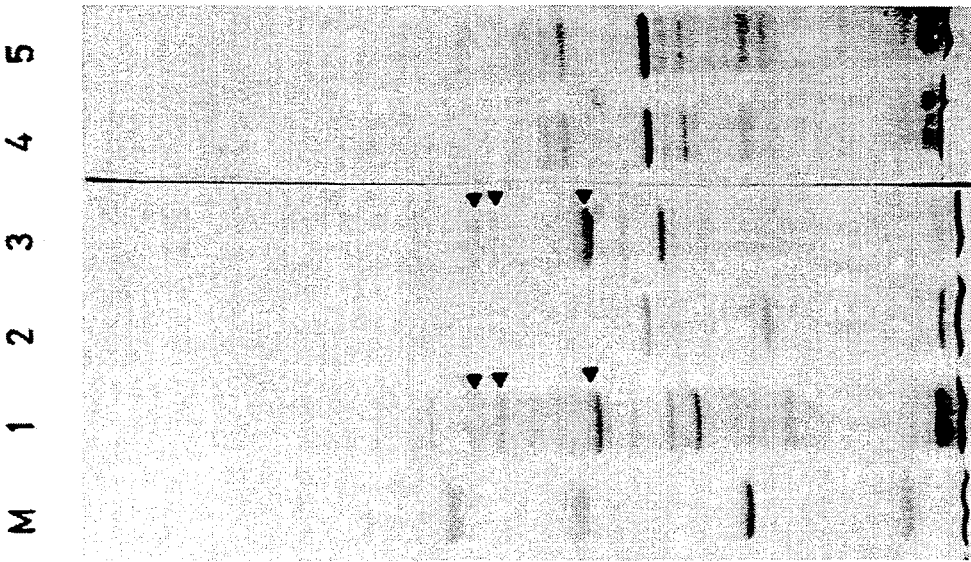
FIGS. 4A and 4B demonstrates inner membrane proteins profiles of EIEC and Shigella.
Figure 4A:
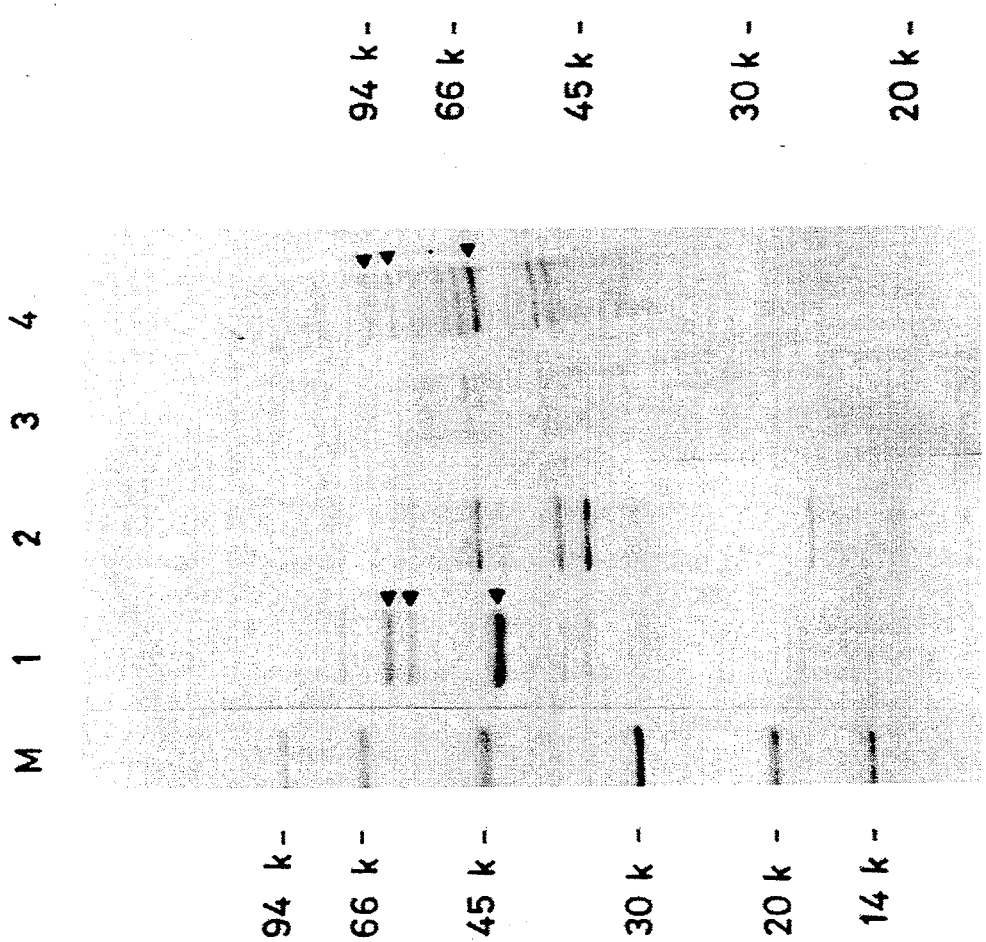
Figure 6A:
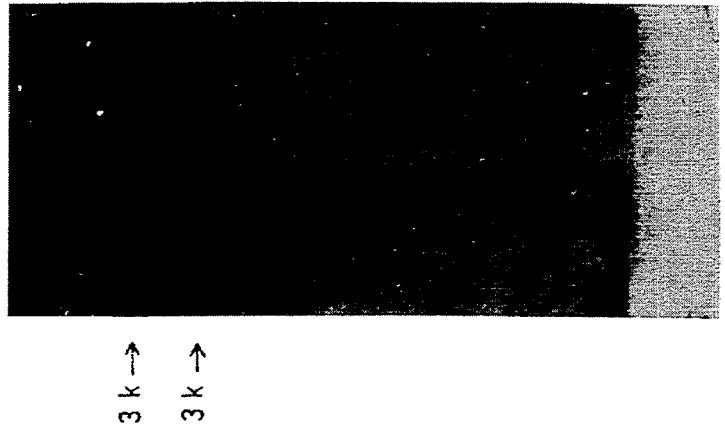
FIG. 6A–6C show recognition of Congo Red induced proteins by sera from patients who had shigellosis.
Figure 6B:
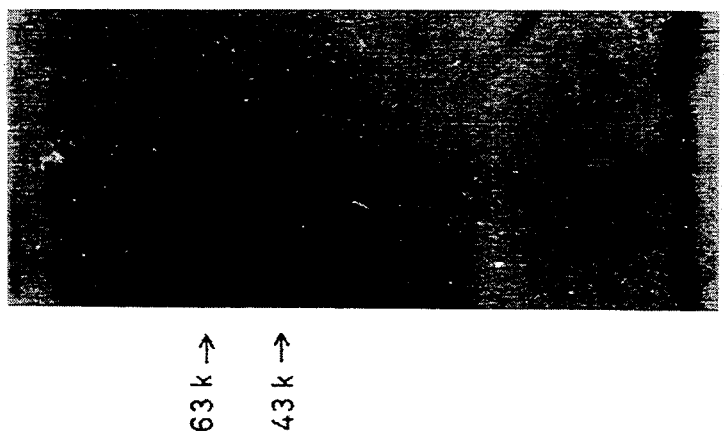
Figure 6C:
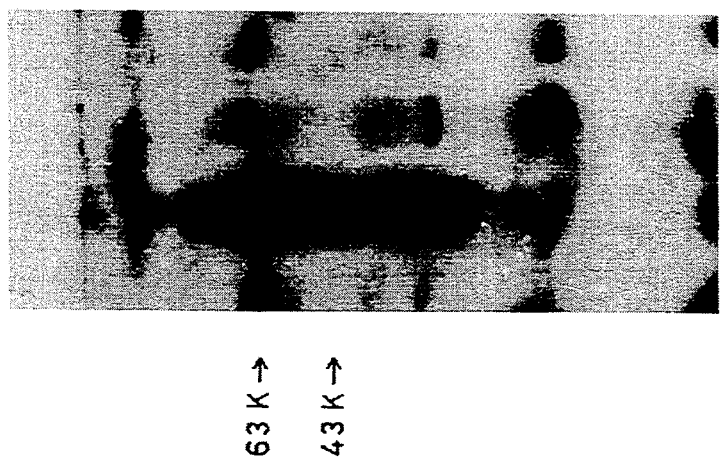

Growth in the presence of CR is another important and necessary factor in the induction of proteins by CR. When CR is added to the cells which are in the stationery phase at 37° C., there is no induction of the said proteins. Only when the CR is added well before the mid-log phase is reached there is induction of these proteins. Again even preincubation with CR does not lead to induction when the cells were subsequently grown at 37° C. in the absence of CR (Example 3, Table 3). At 42° C. the dye enters the cytoplasm as much as that at 37° C. but the proteins are not induced (Example 2, FIG. 3). Even after 18 hours there is no induction of the said proteins when the cells grown at 42° C. to stationary phase in the presence of CR are returned to 37° C. However, a small inoculum of the cells grown at 42° C., when again grown at 37° C. in the presence of CR readily shows induction of these proteins. This also shows that the lack of induction by CR at 42° C. is a phenotypic change rather than a genotypic one.

iv. Detection of Shigella in the infected epithelial cells by indirect immunofluorescence with 43 and 63 KDa specific antisera The induction of specific membrane proteins of Shigella was tested in in vivo models of invasion. Henle 407 intestinal cell line was infected with S.flexneri grown in the absence of CR. By immunofluorescence staining using antisera against 43 KDa and 63 KDa proteins it was demonstrated that the levels of the said proteins in the intracellular bacteria were enhanced in response to invasion of the host cells (Example 5, FIG. 5). In an alternative assay for determining virulence wherein the conjuctival sacs of guinea pigs were infected with Shigella leading to keratoconjunctivitis, bacteria within the epithelial cells showed enhanced levels of the said proteins (Example 5, FIG. 5).

v. Presence of antibodies for 63 KDa, 58 KDa and 43 KDa proteins in sera of convalescent Shigellosis patients The three proteins described earlier are recognised by the convalescent sera from patients who suffered from shigellosis and hence it is concluded that these proteins are relevant to the disease. The immunoblots of the Shigella inner membrane protein (Example 6, FIGS. 6A–6C) clearly shows that the convalescent sera from the patient recognises the 63 KDa, 58 KDa and 43 KDa proteins. The fact that convalescent sera of patients who had suffered from shigellosis caused by either S.dysenteriae or S.sonnei are able to recognise the same set of proteins from S.flexneri 2a show that there is a high degree of similarity between the three species of Shigella. Moreover, the sera are able to recognise the same set of CR inducible proteins in EIEC. Inner membrane protein profiles of the S.dysenteriae and EIEC grown in CR containing medium looks strikingly similar (Example 4, FIGS. 4A and 4B). These facts suggest that the CR induced proteins are important in the pathgenesis of Shigella and EIEC. The ability of CR to induce these virulence associated proteins will be comparable to what is happening in the in vivo situation.

vi. Description of a diagnostic procedure for the detection of virulent invasive bacteria The inventors exploit the above observations and facts to develop a specific diagnostic method for virulent Shigella and EIEC or related invasive pathogens. The method also gives useful information on the antibiotic sensitivity of the pathogen/s. For the sake of highest sensitivity possible, the most abundantly induced protein, namely, the 43 KDa protein was chosen.

The Diagnostic procedure utilizes the following steps:

1. Growing bacteria for a sufficient length of time at least for about 6 hours and upto about 24 hours in a suitable medium containing CR in an amount not lower than 0.0001% w/v preferably not lower than 0.001% w/v but not higher than 0.1% w/v, a preferred concentration being 0.01% w/v.

2. Collecting bacteria, suitably by centrifugation, and releasing the proteins by lysis, suitably using 1% w/v Sodium lauryl sarkosyl or sodium lauryl sarcosine.

3. Coating the lysate onto suitable adsorptive surfaces such as polystyrene as in microtitre plates or tubes and blocking unused surfaces with a non-interfering protein such as bovine serum albumin (BSA).

4. Reacting the coated surface described above, with a first antibody/antibodies against the CR induced protein/s followed by adequate washing steps to remove unbound first antibody/antibodies.

5. Detecting the bound first antibody/antibodies with a second antibody which is raised against the first antibody/antibodies and conjugated to a label, e.g. a reporter enzyme such as horse radish peroxidase conjugated antirabbit IgG.

6. The presence of Shigella and/or other invasive bacteria are detected by assaying for the label, e.g. the reporter enzyme. The method is very sensitive being able to detect as low as $10^2$ organisms even when they are present along with other commensal organisms which may be present in the order of $10^6$ or above (Example 7a, Table 4). Among 17 different enteropathogens tested the methods specifically detected virulent Shigella species and EIEC (Example 7a, Table 5). When Shigella was grown in the presence of pre-determined amounts of an antibiotic in the medium containing CR, and then treated in the manner described in the above diagnostic procedure, the antibiotic sensitivity could be obtained (Example 8, Table 7) The intracellular uptake of CR by virulent Shigella or other invasive bacteria can also be adapted for the detection of these pathogens.

A more efficient method that employs fewer steps compared to the one described above utilises the following steps to detect Shigella and EIEC.

1. Growing the bacteria in the presence of CR as previously described in Step 1 and releasing the proteins by lysis as in Step 2.

2. Coating the antibodies against CR induced protein/s onto suitable adsorptive surfaces such as polystyrene as in microtitre plates or tubes and blocking unused surfaces with a non-interfering protein such as bovine serum albumin (BSA).

3. Reacting the coated surface described above, with the bacterial lysate followed by adequate washing steps to remove unbound bacterial protein/s in the lysate.

4. Detecting the captured CR induced protein/s from the bacterial lysate with the same antibodies as in step 2, but conjugated to a label, e.g. a reporter enzyme such as horse radish peroxidase.

5. The presence of Shigella and/or other invasive bacteria are detected by assaying for the label, e.g. the reporter enzyme. Example 7a describes the efficacy of the diagnostic test performed as above.

Eventhough the examples given in this specification relate to the utilization of induction of 43 KDa proteins, it is under stood that any of the other induced proteins could be used in this procedure. The described method could also be used to detect Shigella or EIEC, from any biological specimen and can be used even in symdromes other than diarrhoea/dysentery.

EXAMPLE 1

Intracellular accumulation of CR by virulent Shigella

Bacteria (virulent and avirulent) were grown routinely over night in presence of 0.01% CR. Bacteria were harvested by centrifugation, washed with 10 mM Hepes buffer pH 7.5 containing 10 mM NaCl, suspended in 10 mM Hepes buffer pH 7.5 at a cell density of $10^9$ cells/ml and disrupted by sonication. After removing the debris and the membrane fractions by centrifugation, the aqueous supernatant was retained as cytosolic fraction. CR in this fraction was measured spectrophotometrically at 480 nm. To determine the amount of CR taken up at different CR concentrations bacteria were grown in medium containing the following final concentrations of 0.001%, 0.002%, 0.005% and 0.01% w/v of CR (FIG. 1). Preparation of cytosolic fractions and measuring the accumulated CR were followed by methods described above. To measure the CR uptake at different growth temperatures the bacteria were grown overnight (approx.18 hours) at appropriate temperatures in presence of 0.01% w/v CR in the medium. Cells were harvested and CR was measured in the cytosolic fractions (FIG. 1). CR uptake during various growth phases was measured by growing bacteria in the presence of CR. Cells were harvested at different time points (0 hour, 40 minutes, 2 hours, 5 hours, 8 hours and 24 hours) and intracellular CR determined in the cytosolic fraction. Data are given in Table 1.

TABLE 1

(Example 1)
Intracellular uptake of CR by Shigella

| Time point (hrs) of harvesting the cells after CR addition | Amount of intracellular CR (μg) per $10^{10}$ cells |
|---|---|
| 2 | Not detectable |
| 5 | 12 |
| 8 | 32 |
| 24 | 45 |

Shigella was grown at 37° C. in a medium containing CR (0.01% w/v). CR was measured spectrophotometrically (480 nm) from the cytosolic fraction.

TABLE 2

(Example 1)
Inherent ability of the cytosolic fraction of Shigella to bind externally added Congo red

| Cytosol prepared from | CR binding μg of CR/100 μg protein |
|---|---|
| Virulent Shigella grown in the absence of CR | 5.2 |
| at 37° C. | |
| at 30° C. | 4.5 |
| Avirulent Shigella grown in the absence of CR at 37° C. | 4.0 |

Gel filtration data on CR binding to high molecular weight fraction of cytosol in bacteria grown in the presence of 0.01% w/v CR.

| Cytosol prepared from | μg of bound CR/100 μg of protein |
|---|---|
| Virulent Shigella grown at 37° C. | 4.1 |
| Virulent Shigella grown at 30° C. | Not detectable |
| Avirulent Shigella grown at 37° C. | 0.76 |

EXAMPLE 2

Alteration of inner membrane protein profile of virulent Shigella by intracellular CR-Induction of 63 KDa, 58 KDa and 43 KDa The sonicate described in example 1 was centrifuged for 2 min at 16,000 xg to remove the debris. The turbid supernatant was centrifuged again at 16,000 xg for 30 minutes to get total membrane pellet. The pellet after washing with 10 mM Hepes buffer pH 7.5 was resuspended in 10 mM Hepes buffer containing 1% w/v Sarkosyl (19). After 1 hour at room temperature with constant agitation the solubilization mix was spun at 16,000 xg for 30 minutes to collect the supernatant as inner membrane fraction, while the pellet was further washed with 10 mM Hepes buffer containing 1% w/v Sarkosyl and then solubilised with sample buffer of Laemelli's electrophoretic system. This represented essentially the outer membrane fraction. The membrane fractions were analysed by SDS-PAGE. Molecular weight estimates were obtained from a gradient gel system containing the known molecular weight markers (FIGS. 2a, 2b) Thermoregulation of the induction of proteins by CR is shown in FIG. 3.

EXAMPLE 3

Evidence for the induction of 63 KDa, 58 KDa and 43 KDa requires growth in the presence of CR As is shown in table 3 below growth of Shiqella in the presence of CR is essential for induction of 63 KDa, 58 KDa and 43 KDa proteins. The organism was grown for 18 hours after the addition of CR at 37° C. The proteins were estimated from densitometric scans of Coomassie blue stained SDS-PAGE gels.

TABLE 3

(Example 3)
Induction of proteins requires growth in the presence of CR

| Time point (min) of addition of CR after inoculation | Maximum amount of protein induced. (μg/100 μg of inner membrane protein) | | |
|---|---|---|---|
| | 63KDa | 58KDa | 43KDa |
| 0 | 7.2 | 4.8 | 15.5 |
| 50 | 6.4 | 3.8 | 12.0 |
| 100 | 6.4 | 4.4 | 11.4 |
| >150 or when the OD of cells >0.5 | NI | NI | NI |
| stationary phase OD of cells >1.0 | NI | NI | NI |
| Preincubation of bacteria with 0.01% w/v CR from 0–8 hours without growth and subsequently grown in the medium without CR | NI | NI | NI |

NI = Not induced

EXAMPLE 4

CR induced proteins are similar in other species of Shiqella and EIEC

FIG. 4 (a) and 4 (b) demonstrates that the inner membrane proteins (63 KDa, 58 KDa and 43 KDa) are induced in an analogous manner in all the species of virulent Shiqella and EIEC tested. However, in non invasive pathogen, enteropathogenic E. coli, no such induction could be discerned.

EXAMPLE 5

Detection of 63 KDa and 43 KDa by indirect immunofluorescence

Bacterial invasion of Henle 407 cells was carried out essentially according to the method of Hale et.al. (17). One hour absorption time and a subsequent 2 hours incubation in the presence of 200 μg/ml of gentamicin was carried out to kill extracellular bacteria. The infected monolayers were then washed with phosphate buffered saline (PBS), air dried and fixed with chilled acetone for 20 minutes. After three washes with PBS and blocking with 3% w/v goat serum in PBS for 30 minutes, specimens were incubated with 43 KDa specific antiserum (1:2000 dilution in PBS containing 1% w/v goat serum) or 63 KDa specific antiserum (1:1000 dilution) for one hour in a humid atmosphere at room temperature. Following three 5 minute washes with PBS, goat anti rabbit IgG-Fluorescein isothiocyanate conjugate (Sigma 1:40 dilution) was added to the cover slips as the second antibody and the coverslips were incubated further for 45 minutes in the dark. The cover slips were then washed with PBS, mounted in buffered glycerol under a glass cover slip and were examined by epifluorescence microscopy. For positive and negative controls Shigella grown in the presence and in the absence of CR were similarly subjected to indirect immunofluorescence using the 43 KDa specific and 63 KDa specific antisera. Sereny test of guinea pig (Keratoconjunctivitis) was carried out as described (2). Conjunctivitis of the cornea developed between 10-24 hours with the virulent strains. For microscopic studies, corneal epithelial cells were scrapped from the eye 10 hour after infection, using opthalmic implements and suspended in PBS. Smears were prepared from the suspension and processed for immunofluorescence staining. FIG. 5 demonstrates the presence of enhanced levels of 43 KDa proteins associated with intracellular bacteria in the infected epithelial cells.

EXAMPLE 6

The convalescent sera from patients who suffered from Shigellosis recognised CR induced proteins.

Membrane proteins separated by SDS-PAGE, were electroblotted onto nitrocellulose (FIG. 6). The blots were blocked with 0.1M Tris HCL, pH 7.5, containing 1M NaCl, 0.01M MgCl, 0.05% v/v Triton X-100 and 3% BSA for 30 min. Human sera (1:100 dilution) or the specific antiserum raised in rabbit against electroeluted 43 KDa membrane protein of Shigella (1:500 dilution) was added in the blocking buffer and incubated for 30 min at room temperature with the blot. The blots were subsequently given four washes of 10 min each with wash buffer (blocking buffer without BSA). Washed blots were incubated with $^{125}$I-labelled Staphylococcal protein A dissolved in blocking buffer for 30 min. After three quick rinses and five washes of 10 min each the blots were exposed to X-ray film overnight or longer. Sera from persons who had no known episode of Shigellosis were used in the present studies, as controls.

EXAMPLE 7

Diagnostic method based on CR induction of the virulence protein 43 KDa.

a. A diagnostic procedure has been developed for the detection of virulent invasive organisms such as Shigella, and EIEC and other related invasive organisms by the method of ELISA (FIG. 7a). Organisms were grown in the presence of CR overnight at 37 C in tryptic soy broth. The overnight cultures were washed with 10 mM Hepes buffer pH 7.4 and suspended in 1% w/v Sarkosyl in the same buffer for one hour at room temperature.

Figure 7B:
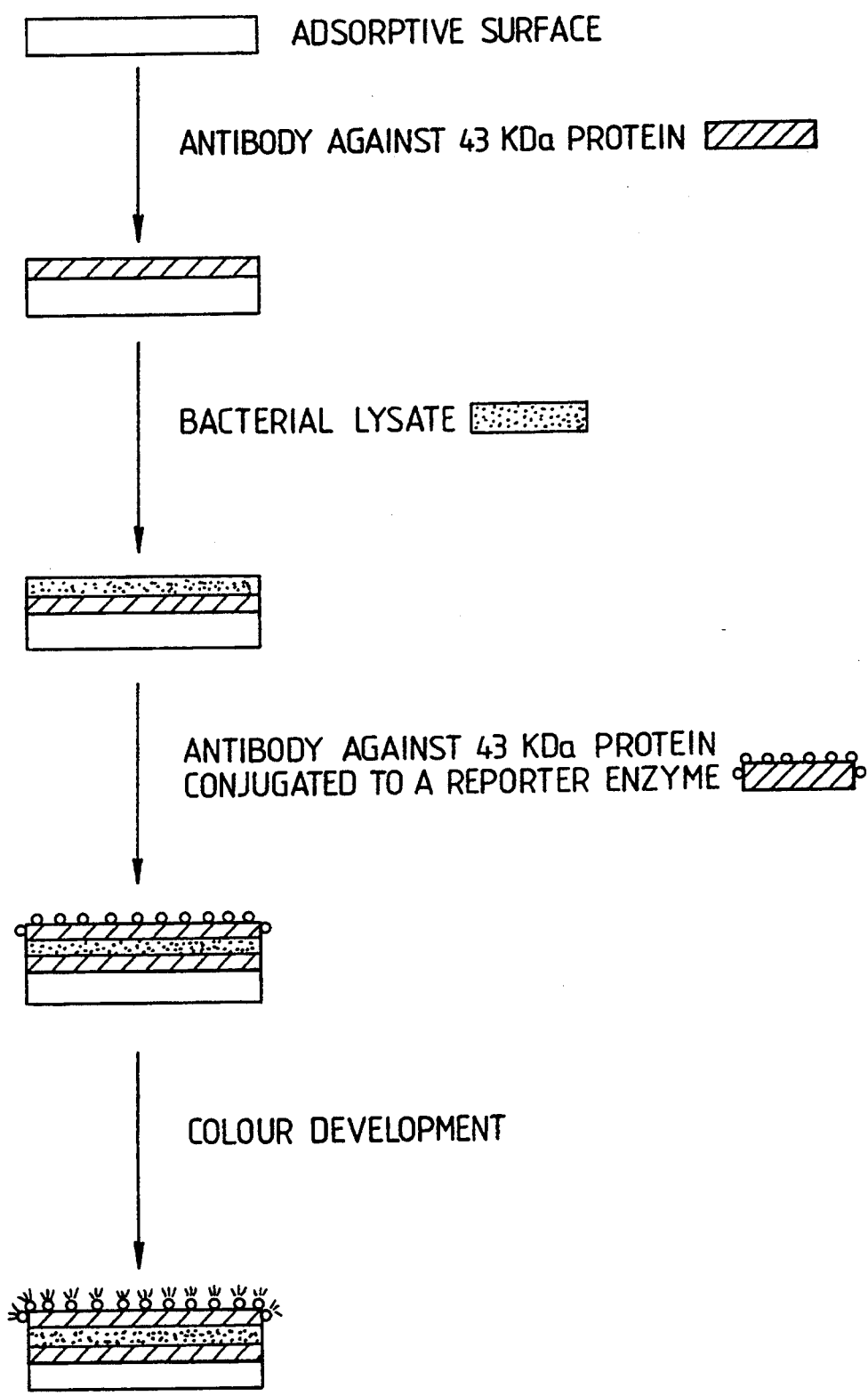

This step facilitates the release of antigens. The lysate is centrifuged and the supernatant used to coat microtitre wells for 15 minutes at 37° C. The wells were blocked with 0.2% w/v BSA in PBS for 15 minutes at 37° C. The ELISA plate was washed 6 times with 0.2% v/v Tween in PBS. The specific 43 KDa antiserum was added to the wells in a 1:1000 dilution and incubated at 37° C. for 15 min. This was followed by 6 washes with PBS - Tween. The anti rabbit IgG peroxidase conjugate was added in a 1:1000 dilution and incubated for 15 minutes at 37° C., again followed by 6 washes with PBS-Tween. The substrate (Ortho-phenylene-diamine) was then added (4 mg/10 ml) along with 0.03% v/v $H_2O_2$ to develop colour in the dark at room temperature for 15 minutes. The reaction was terminated by addition of 50 μl of $3NH_2SO_4$ and the plate read in a ELISA reader at 459 nm. This procedure was found to be very specific for Shigella and EIEC, both of which gave a high optical density value when compared to the non invasive strains of bacteria (Table 4 & 5). The advantage of this procedure is that a detection can be made within 24 hours of receiving the sample.

b. An alternative direct ELISA procedure that employs less steps and is more sensitive compared to the indirect ELISA described, above has been developed (FIG. 7b, Table 6). The method involved capturing the 43 kDa antigen of the virulent organism on an antibody coated surface followed by detection of the bound 43 kDa antigen with the horse radish peroxidase conjugated 43 kDa antibody.

STEPS

1. Each microtitre well was coated with 20 ng of IgG fraction of the 43K antiserum, overnight 4° C.
2. Free sites on the plastic surface were blocked using 0.2% BSA in PBS (Phosphate buffered saline) for 15 minutes at 37° C. Excess BSA was washed off with PBS-tween (PBST, 0.05% Tween in PBS).
3. Bacteria in the stool samples were grown in the presence of Congo red at 37° C. and the Sarkosyl solubilized extract was allowed to bind the coated plates for 15 minutes at 37° C.
4. After washing off the free antigens with PBST, the 43K antibody horse radish peroxidase conjugate (prepared by standard procedures) was allowed to bind the captured 43K antigen for 15 minutes at 37° C.
5. The wells were washed with PBST and the colour was developed and reaction terminated as explained in example 7a.

EXAMPLE 8

The diagnostic method that gives the antibiotic resistance or sensitivity pattern of Shigella Organisms were grown in the presence of CR and in the presence or absence of antibiotics, such as kanamycin, ampicillin, tetracycline, streptomycin and gentamicin separately each at a concentration of 50 μg/ml. The procedure from then on was essentially the same as described in Example 7a. This procedure showed that the Shigella strain used was resistant to tetracycline, ampicillin and streptamycin but sensitive to kanamycin and gentamycin. The optical density values for Shigella grown in the presence of these antibiotics (tetracycline, ampicillin and streptamycin) were closely comparable to that grown in the absence of any antibiotics. The procedure will enable the physician to choose a suitable antibiotic for treatment. The above results have been presented in Table 7.

TABLE 4

(Example 7a)
ELISA WITH SHIGELLA, COMMENSAL ORGANISMS AND SHIGELLA IN THE PRESENCE OF COMMENSAL ORGANISMS (Normal flora obtained from stool samples of healthy person)

| Organism | Optical density |
|---|---|
| $10^9$ Shigella | 1.850 |
| $10^9$ Comm. org | 0.000 |
| Number of + Number of Shigella commensal Org. | |

TABLE 4-continued (Example 7a)
ELISA WITH SHIGELLA, COMMENSAL ORGANISMS AND SHIGELLA IN THE PRESENCE OF COMMENSAL ORGANISMS (Normal flora obtained from stool samples of healthy person)

| Organism | | Optical density |
|---|---|---|
| $10^8$ | $10^6$ | 1.965 |
| $10^7$ | $10^6$ | 1.868 |
| $10^6$ | $10^6$ | 1.564 |
| $10^5$ | $10^6$ | 1.288 |
| $10^4$ | $10^6$ | 1.258 |
| $10^3$ | $10^6$ | 0.935 |
| $10^2$ | $10^6$ | 0.778 |

TABLE 5

(Example 7a)
Specificity of diagnostic-test method

| ORGANISMS | Optical density |
|---|---|
| Shigella flexneri 2a (virulent) | 1.105 |
| Sh. flexneri 2a (Virulent) | 1.074 |
| Sh. dysenteriae-3 (virulent) | 1.218 |
| Sh. dymenteriae-1 (virulent) | 1.108 |
| Enteroinvasive E. coli (virulent) | 1.127 |
| Sh. flexneri 2a (avirulent) | 0.196 |
| Sh. sonnei (avirulent) | 0.372 |
| Sh. boydii (avirulent) | 0.225 |
| Pleisomonas shigelloides | 0.184 |
| Sal 'O' Group B | 0.212 |
| Vibrio choleras | 0.172 |
| Salmonella typhimurium | 0.387 |
| Citrobacter | 0.240 |
| Proteus | 0.150 |
| Aeromonas | 0.237 |
| Staphylococcus aureus | 0.220 |
| E. coli (noninvasive) | 0.300 |
| Pseudomonas | 0.170 |
| Klebsiella | 0.250 |
| Enteropathogenic E. coli (EPEC) | 0.306 |

TABLE 6

(Example 7b)
Sandwich ELISA of Shigella, Enteroinvasive E. coli and other strains of invasive and non-invasive bacteria:

| Strains | ELISA reading (O.D value at 459 nm) |
|---|---|
| 1. Shigella flexneri2a (Virulent) | 1.325 |
| 2. Shigella flexneri Y (Virulent) | 1.318 |
| 3. Shigella flexneri 1D (Virulent) | 1.308 |
| 4. Shigellg dysenteriae (Virulent) | 1.290 |
| 5. Shigella boydii (Virulent) | 1.067 |
| 6. Shigella sonnei (Virulent) | 0.965 |
| 7. Enteroinvasive E. coli (EIEC) | 1.168 |
| 8. Campylobacter | 0.058 |
| 9. Yersinia | 0.047 |
| 10. Salmonella | 0.120 |
| 11. Normal stool organisms | 0.046 |
| 12. E. coli (non-invasive) | 0.090 |
| 13. Aviruient Shigella (Multidrug resistance) | 0.116 |
| 14. Enteropathogenic E. coli (EPEC) | 0.154 |
| 15. Aeromonas | 0.184 |
| 16. Citrobacter | 0.030 |
| 17. Vibrio cholerae | 0.038 |
| 18. Poeudomonas | 0.075 |
| 19. Proteus | 0.181 |
| 20. Klebsiella | 0.053 |

TABLE 7

(Example 8)
Antibiotic sensitivity pattern of virulent Shigella flexneri 2a

| Shigella | Known sensitivity | Optical density | Derived sensitivity |
|---|---|---|---|
| No antibiotics | — | 1.438 | — |
| Ampicillin | R | 1.293 | R |
| Tetracycline | R | 1.071 | R |
| Streptomycin | R | 1.256 | R |
| Kanamycin | S | 0.374 | S |
| Gentamicin | S | 0.121 | S |

R = Resistant
S = Sensitive

Figure Legends

FIG. 1. Uptake of CR by virulent and avirulent Shigella

Virulent Shigella takes up Congo red intracellularly at 37° C. and 42° C. (0—0; Δ—Δ) while at 30° C. (0—0) there is no significant level of Congo red in the cytosol. The amount taken in exhibits a linear relationship with respect to the dye concentration in the medium. The organism is able to take up as much as 15 μg of the dye per $4 \times 10^9$ cells at a dye concentration of 100 μg/ml in the medium. In contrast avirulent Shigella (Δ—Δ) takes up only 5 μg of the dye under similar conditions. The induced levels of 43 KDa proteins (□—■) correlates well with the increased accumulation of Congo red in the cytosol; however, the maximum induction which can be obtained (150 μg/mg of protein) is reached at 50 μg/ml of dye concentration in the medium. Further increases in the dye concentration does not affect the level of the 43 KDa protein.

Figure 2A:
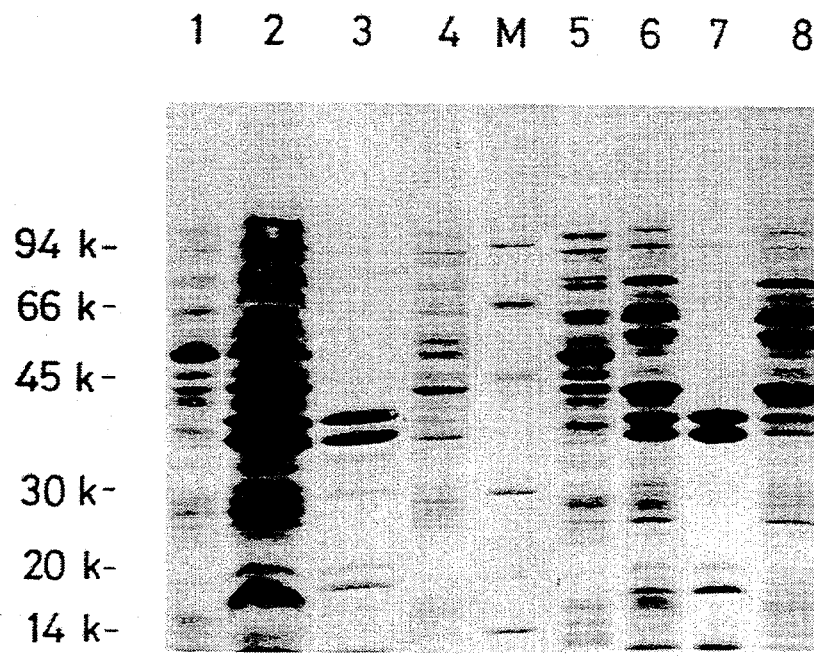
FIGS. 2A and 2B show SDS-PAGE analysis of cytosol and membrane fractions of virulent and avirulent Shigella.
Figure 2B:
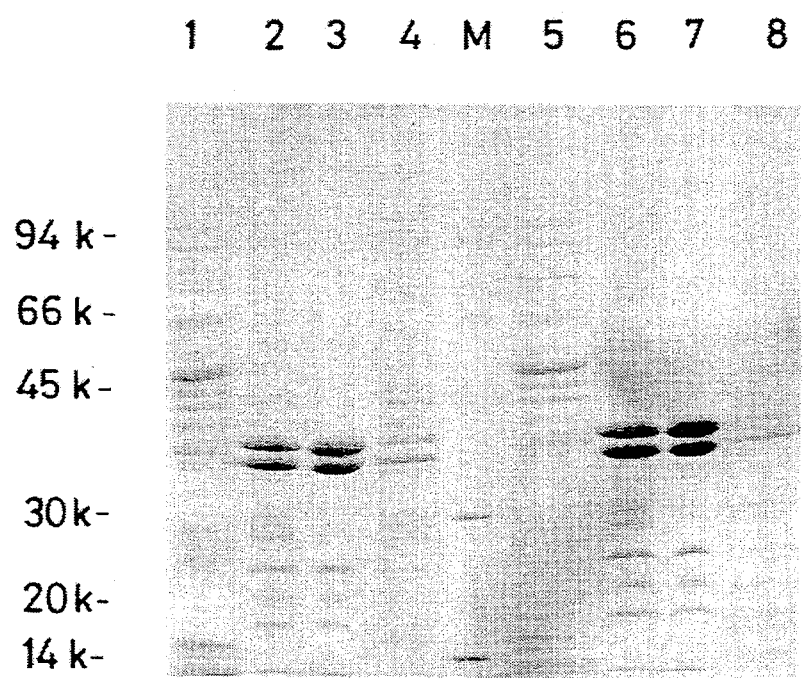
Figure 3:
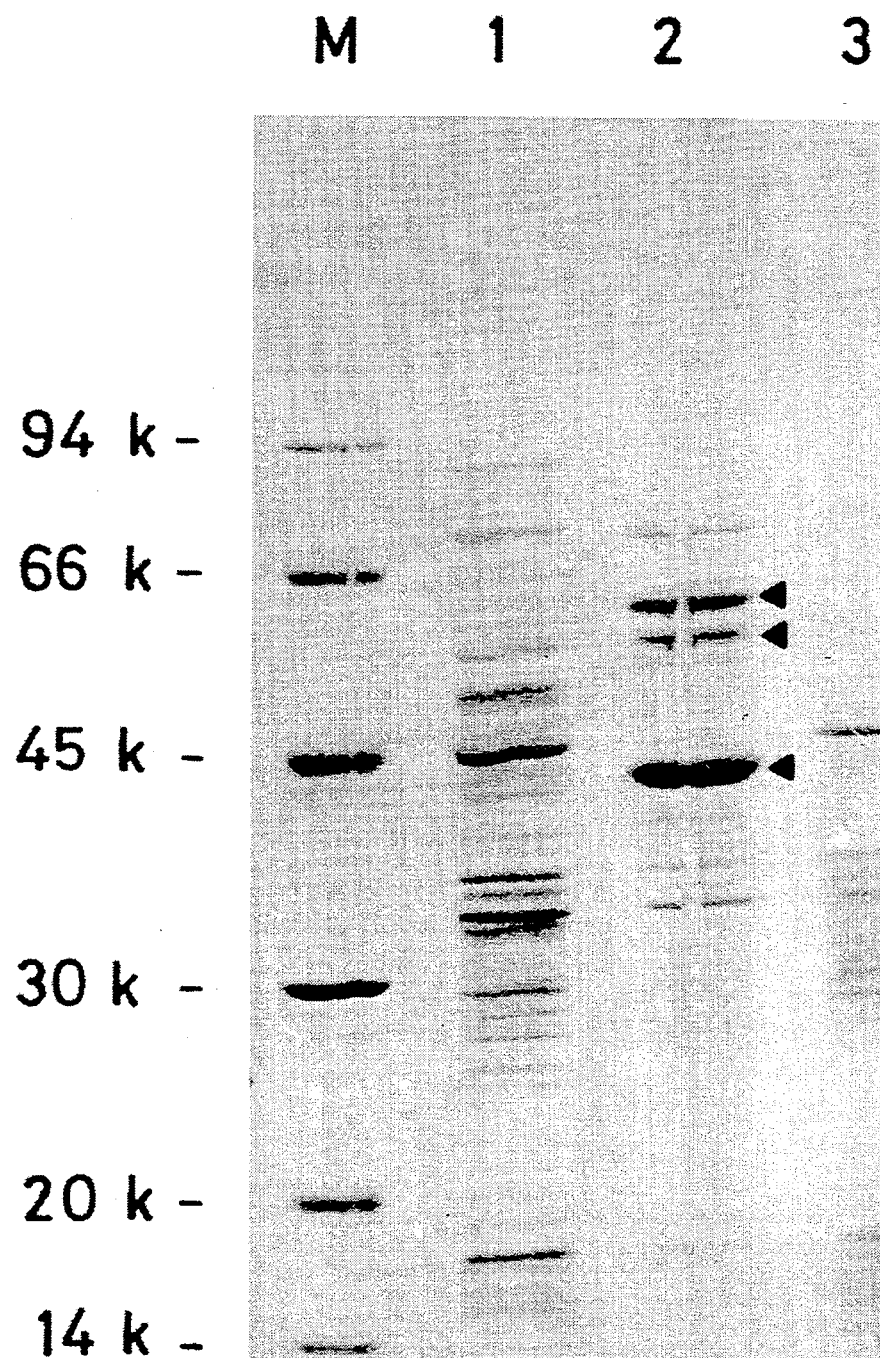
FIG. 3 shows SDS-PAGE analysis of soluble membrane proteins of virulent *S. flexneri* grown in the presence of Congo Red at different temperatures.

FIGS. 2A and 2B: SDS-PAGE (9-15% gradient gel) analysis of cytosol and membrane fractions of S.flexneri 2a. Panel A, virulent Shigella grown in the absence (1-4) and in the presence (5-8) of CR at 37° C.). Cytosol (1,5), total membranes (2,6), Sarkosyl-insoluble membrane (3,7) and Sarkosyl-soluble membrane (4,8). Panel B, avirulent Shigella grown in the absence (1-4) and in the presence (5-8) of CR at 37° C. Cytosol (1,5), total membranes (2,6), Sarkosyl-insoluble membrane (3,7) and Sarkosyl-soluble membrane (4,8). Molecular weight markers (M). indicates the CR regulated proteins. Protein loaded per lane: 50 μg (lanes A 3, 7; B 3,7); 100 μg (lanes A 1,4-6, 8; B 1,2,4-6, 8); 150 μg (lane A 2).

FIG. 3: SDS-PAGE (9-15% gradient gel) analysis of Sarkosylsoluble membrane proteins (100 μg/lane) of virulent Shigella flexneri 2a grown in the presence of CR at 30° C. (lane 1), 37 C (lane 2) and 42° C. (lane 3). Molecular weight markers (M). Only at 37° C. regulated proteins (▲) are seen.

FIG. 4: Membrane protein profiles of invasive and non-invasive enteropathogens. Panel A, SDS-PAGE (9-15% gradient gel) analysis of Sarkosyl-soluble membrane proteins (100 μg/lane) of virulent Shigella flexneri 2a grown in the presence (lane 1) and in the absence (lane 2) of CR at 37° C; EIEC, grown in absence (lane 3) and presence (lane 4) of CR at 37° C. Panel B, SDS-PAGE (9% gel) analysis of Sarkosylsoluble membrane proteins (100 μg/lane) of virulent Shigella flexneri 2a grown in the presence of CR (lane 1); Shigella dysenteriae 1 grown in the absence (lane 2) and in the presence of CR (lane 3) at 37° C.; Enteropathogenic E. coli grown in the absence (lane 4) and in the presence (lane 5) of CR at 37° C. This is a composite gel picture. Only invasive organisms exhibited regulation of membrane proteins.

FIG. 5: Invasion of epithelial cells by *S. flexneri* 2a and detection of the 43 KDa protein. Panel A, Henle 407 monolayers and corneal epithelial cells from guinea pigs were fixed in methanol and Giemsa stained. Details are given in example 5. a, infected Henle 407 cells incubated for 120 min in the presence of gentamicin; b,c, corneal epithelial cells from uninfected and infected eye, respectively. Panel B: a,b,c, immunofluorescence labelling of respective duplicate samples of Panel A. Panel C, positive and negative controls for immunofluorescence experiments: (a,b), Shigella grown in the presence and in the absence of CR, respectively; c, infected Henle 407 monolayers treated with normal rabbit serum as the primary antibody. Details of immunofluorescence experiments are given in Example 5. First antibody used in all these studies was 43 KDa antiserum. Similar results were obtained when 63 KDa antiserum was used as the primary antibody (data not shown).

FIG. 6: Recognition of Congo Red induced proteins by sera from convalescent patients Western blots of inner membrane fractions of *Shigella flexneri* 2a were treated with the convalescent sera from patients who suffered from shigellosis. The autoradiograms show that the sera reacted with the induced proteins 63 KDa, 58 KDa and 43 KDa. The level of these proteins are low when not induced by CR (lane 1 *S. flexneri* 2a), even the basal levels are not seen when the virulent Shigella was grown at non-permissive temperature (30° C.) (lane 3 of each panel) or in the avirulent strain (lane 4 of each panel). *S. flexneri* 2a convalescent serum was obtained from a child, *S. dysenteria* and *S. sonnei* sera were obtained from adults. Sera were used in the experiment at a dilution of 1:100.

FIG. 7a and 7b are schematic illustrations of the diagnostic procedures described in Examples 7a and 7b, respectively.

References

1. LaBrec, et. al (1964), J. Bacteriol. 88, 1503–1518.
2. Sasakawa, et. al. (1986), Infec. Immun. 51, 470–475.
3. Payne, S. M., et. al (1977), Infec. Immun. 18, 94–98.
4. Kopecko, D. J., et. al. (1985), Current Topics in Microbiology and immunology, 118, 71–95
5. Sansonetti, P. J., et. al. (1982), Infec. Immun. 35, 852–860.
6. Sansonetti, P. J., et. al. (1983), Infec. Immun. 39, 1392–1402.
7. Sakai, T. et. al. (1986) Infec. Immun, 51, 476–482.
8. Buysse, J. M., et. al. (1987) J. Bacteriol. 169, 2561–2569.
9. Makino, S., et. al. (1986), Cell, 46, 551–555.
10. Maurelli, A. T., et. al. (1988), PNAS, 85, 2820–2824.
11. Maurelli, A. T., et. al. (1984), Infec. Immun. 43, 195–201.
12. Maurelli, A. T., et. al (1984), Infec. Immun, 43, 397–401.
13. Ishiguro, E. E., et. al. (1985) J. Bacteriol. 164, 1233–1237.
14. Daskaleros, P. A., et. al. (1987) Infec. Immun. 55, 1393–1398.
15. Sakai, T., et. al. (1986) Infec. Immun. 54, 395–402
16. Carlone, G. M., et. al. (1986) J. Clin. Microbiol. 24, 332–334.
17. Hale, T. L., et. al. (1979) Infec. Immun. 24, 887–894.

We claim:

1. A method of detecting the presence of virulent enteroinvasive *E. coli* or Shigella bacteria in a sample of bacteria comprising:
   culturing the bacteria in the presence of Congo Red for a time and at a temperature sufficient for Congo Red to cause the production of virulence-associated proteins by the bacteria,
   collecting the bacterial cells and releasing the Congo Red-induced virulence-associated proteins, and
   detecting the presence of the Congo Red-induced virulence-associated proteins wherein the presence of the Congo-Red-induced virulence-associated proteins is indicative of the presence of virulent enteroinvasive *E. coli* or Shigella in the sample of bacteria.

2. The method according to claim 1 wherein the Congo Red-induced virulence-associated proteins are specific for the detection of virulent Shigella species.

3. The method according to claim 2 wherein the Congo Red-induced virulence-associated proteins have an apparent molecular weight of 63 KDa, 58 KDa or 43 KDa.

4. The method according to claim 1 wherein the Congo Red-induced virulence-associated proteins are specific for the detection of virulent enteroinvasive *E. coli*.

5. A method for detecting virulent enteroinvasive *E. coli* or Shigella bacteria in a sample of bacteria which comprises:
   a. growing the sample of bacteria in a growth medium containing Congo Red as an induction triggering factor for a time and at a temperature sufficient to cause the production of Congo Red-induced virulence-associated proteins to take place,
   b. collecting the bacterial cells and releasing the Congo Red-induced virulence-associated proteins by lysis,
   c. solubilizing the Congo Red-induced virulence-associated proteins to form a lysate,
   d. coating the lysate containing the solubilized proteins onto an adsorptive surface,
   e. blocking the non-specific binding sites on the surface with a non-interfering protein,
   f. contacting the surface with first antibodies which specifically bind to the Congo Red-induced proteins present on the surface for a time and under conditions sufficient to form complexes thereon,
   g. contacting the surface having the complexes thereon with second antibody which is conjugated to a detectable label and which specifically binds to the first antibodies present in the complexes for a time and under conditions sufficient to form labeled complexes, and
   h. detecting the presence of the labeled complexes on the surface as an indication of the presence of virulent enteroinvasive *E. coli* or Shigella bacteria.

6. A method for detecting virulent enteroinvasive *E. coli* or Shigella bacteria in a sample of bacteria which comprises:
   a. growing the sample of bacteria in a growth medium containing Congo Red as an induction triggering factor for a time and at a temperature sufficient to cause the production of Congo Red-induced virulence associated proteins to take place,
   b. collecting the bacterial cells and releasing the Congo Red-induced virulence associated proteins by lysis to form a bacterial lysate, c. contacting the bacterial lysate with a surface having present thereon antibodies which specifically bind to the Congo Red-induced virulence-associated proteins for a time and under conditions sufficient to form complexes on the surface, wherein the surface is obtained by coating an adsorptive surface with the antibodies and then applying a non-interfering protein to block non-specific binding sites, d. contacting the surface having complexes thereon with labeled antibodies which specifically bind to the Congo-Red induced virulence-associated proteins present in the complexes for a time and under conditions sufficient to form labeled complexes on the surface, e. detecting the presence of the labeled complexes on the surface as an indication of the presence of virulent enteroinvasive *E. coli* or Shigella bacteria.

7. A method for detecting virulent enteroinvasive *E. coli* or Shigella bacteria in a sample of bacteria which comprises:

a. growing the sample of bacteria in a growth medium containing Congo Red as an induction triggering factor for a time and at a temperature sufficient to cause the production of Congo Red-induced virulence associated proteins to take place, b. collecting the bacterial cells and releasing the Congo Red-induced virulence associated proteins, c. solubilizing the Congo Red-induced virulence-associated proteins, d. contacting the Congo Red-induced virulence-associated proteins with a surface having present thereon antibodies which specifically bind Congo Red-induced virulence-associated proteins for a time and under conditions sufficient to form complexes on the surface, wherein the surface is obtained by coating the antibodies onto an adsorptive surface and blocking the non-specific binding sites on the surface with a non-interfering protein, e. contacting the surface having complexes thereon with a labeled antibody which specifically binds to the Congo-Red induced virulence-associated proteins bound onto the surface for a time and under conditions sufficient to form labeled complexes on the surface, f. detecting the presence of the labeled complexes on the surface as an indication of the presence of virulent enteroinvasive *E. coli* or Shigella bacteria.

8. The method according to claim 5, 6 or 7 wherein the virulent bacteria are virulent species of Shigella.

9. The method according to claim 5, 6, or 7 wherein the virulent bacteria are virulent enteroinvasive *E. coli*.

10. The method according to claim 5, 6 or 7 wherein Congo Red (CR) is used in a concentration of from 0.0001% (w/v) to 0.1% (w/v).

11. The method according to claim 5, 6 or 7 wherein the sample of bacteria is grown for a period of from about 2 to about 24 hours.

12. The method according to claim 5, 6 or 7 wherein sodium lauroyl sarcocine is used for lysis and solubilization.

13. The method according to claim 5, 6 or 7 wherein a sample of Shigella is grown at 37° C.

14. The method according to claim 5, 6 or 7 wherein CR is used at a concentration of 0.01% (w/v).

15. The method according to claim 5, 6 or 7 wherein the Congo Red-induced virulence-associated proteins in the virulent enteroinvasive *E. coli* or Shigella have apparent molecular weights of 63 KDa, 58 KDa or 43 KDa.

16. The method according to claim 5, 6 or 7 wherein the sample of enteroinvasive *E. coli* is grown at 37° C.

17. The method according to claim 5, 6 or 7 wherein the sample of bacteria is grown in the presence of an antibiotic.

* * * * *